United States Patent [19]

Homan

[11] 4,031,890

[45] June 28, 1977

[54] SAFETY I. V. INJECTOR

[75] Inventor: Gerlof Homan, St. Louis, Mo.

[73] Assignee: Survival Technology, Inc., Bethesda, Md.

[22] Filed: Jan. 14, 1976

[21] Appl. No.: 648,972

[52] U.S. Cl. .............................. 128/215; 128/218 R; 128/221

[51] Int. Cl.² ........................................ A61M 5/32

[58] Field of Search ........ 128/214 R, 214.2, 218 R, 128/218 C, 218 N, 215, 221

[56] References Cited

UNITED STATES PATENTS 2,402,306 6/1946 Turkel ................................. 128/215

FOREIGN PATENTS OR APPLICATIONS 453,877 4/1913 France ................................. 128/221

73,079 8/1953 Netherlands ................... 128/218 R

Primary Examiner—Dalton L. Truluck
Attorney, Agent, or Firm—Witherspoon, Lane & Hargest

[57] ABSTRACT

An I.V. injector having a cylindrical barrel open at one end and closed at the other end by sealing means, a cannula mounted on the closed end outwardly from the sealing means, a plunger slidably carried in the open end of the barrel, a chamber formed in the barrel between the plunger and the sealing means, said chamber being adapted to receive a high concentrate I.V. medicament, and a safety member on the closed end of the barrel to render the injector impractical for use in intravenous injection of the I.V. medicament into a patient.

3 Claims, 2 Drawing Figures

SAFETY I. V. INJECTOR

SUMMARY OF THE INVENTION

This invention relates to an I.V. injector having a concentrated medicament therein and safety means on the injector for preventing the use of the injector to intravenously inject the concentrated medicament into a patient.

In modern hospital practice, highly concentrated I.V. additives are used. These additives are generally medicaments contained in disposable injector units which greatly resemble conventional disposable prefilled syringe units containing medicament fpr subcutaneous, intravenous or intramuscular injection into a patient. The injections of a highly concentrated I.V. additive into a patient could have very bad reactions and possibly cause death. Obviously, the most serious situation would be that brought about by the introduction of the concentrated additive directly into the patient's blood stream by intravenous injection. Thus, there is a need for means to prevent the misuse of an I.V. injector as a conventional intravenous syringe unit.

In view of the foregoing, it is an object of this invention to provide an I.V. injector with safety means such that it will be impractical for the I.V. injector to be used as a syringe for direct injection into a patient.

It is another object of this invention to provide an I.V. injector with a safety disc on its cannula end so that the angle of entry of the cannula with respect to the patient's skin surface and blood vessel is greater than 45° thus making injection impractical and thus prevent misuse of the I.V. injector.

The above and other objects and advantages will become more apparent when taken in conjunction with the following detailed description and drawing.

IN THE DRAWING

FIG. 1 is a view on an intravenous injector positioned at the proper angle for introduction into the patient, and FIG. 2 is a view of an I.V. injector containing concentrated medication and provided with the safety feature of this invention.

DETAILED DESCRIPTION OF THE INVENTION

Figure 1:
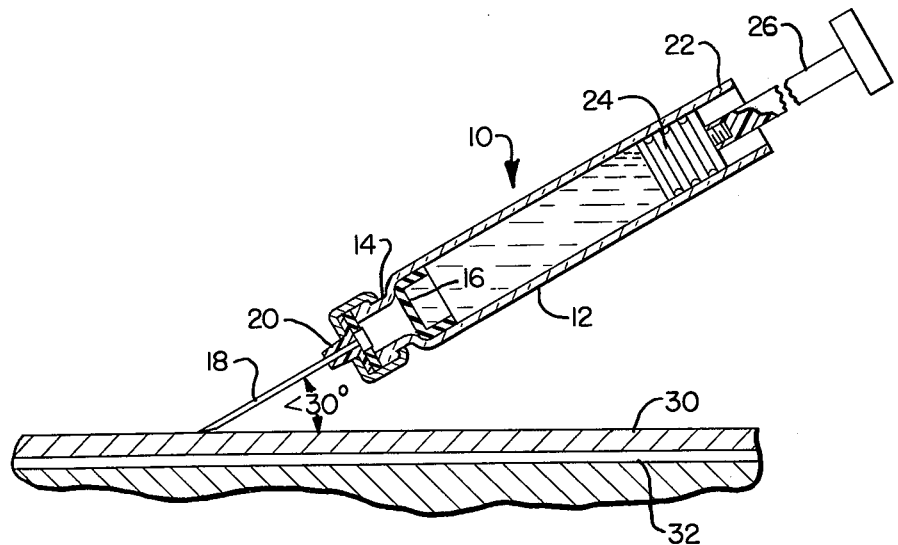

FIG. 1 shows a conventional intravenous syringe unit 10 comprising a glass barrel 12 having a necked end 14 closed by internal sealing means 16. The necked end 14 mounts a cannula 18 which is secured to said end by conventional hub means 20. The open end 22 of the glass barrel 12 is provided with a slidable plunger 24 connected to a suitable plunger rod 26. A medicament chamber 28 is formed between the sealing means 16 and plunger 24.

As shown in FIG. 1, the cannula 18 is positioned ready for entry into the patient's skin surface 30 and then blood vessel 32. It should be noted that the included angle formed between the cannula 18 and the patient's skin surface as well as the blood vessel 32 is less than 30°. The accepted procedure for successfully performing an intravenous injection includes the limitation that the injection needle must be positioned such that the included angle between the cannula and the longitudinal blood vessel is preferably less than 30°. In the event that the angle of injection is significantly more than 30° there is a strong possibility that the blood vessel may be completely pierced.

Figure 2:
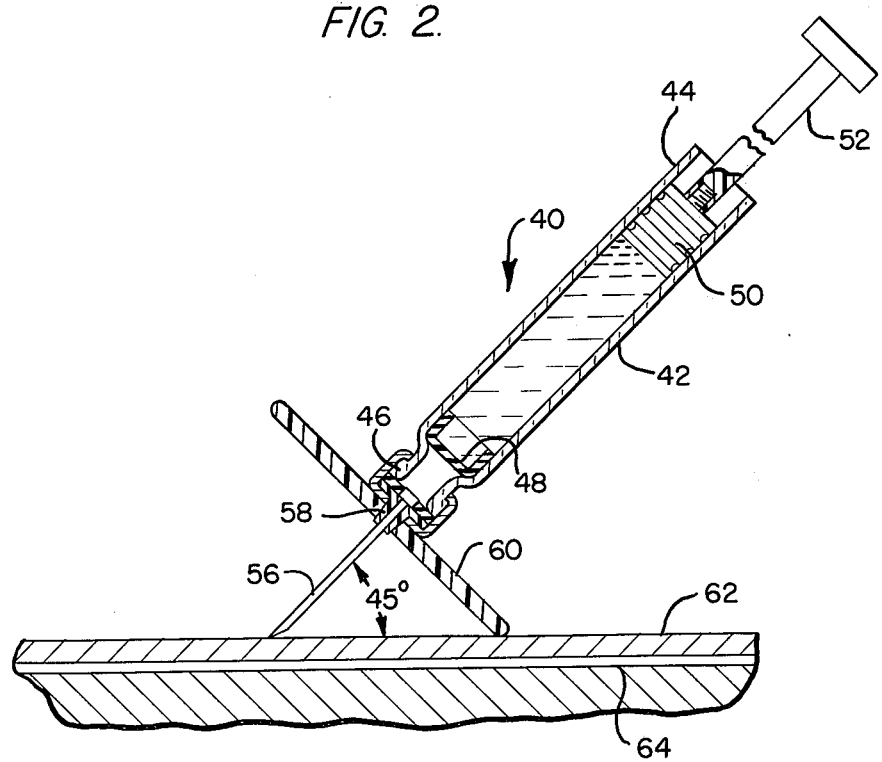

In order to make certian that an I.V. injector is not accidentally used for intravenous injection into a patient, the safety arrangement illustrated in FIG. 2 has been invented. In this figure, there is shown an I.V. injector 40 comprising a cylindrical glass barrel 42 having an open end 44 and a closed end 46. The closed end is provided with a sealing means 48 while the open end slidably receives a plunger 50 having a plunger rod 52 connected thereto. A medicament chamber 54 is formed between the plunge 50 and sealing means 48 and is adapted to receive a concentrated I.V. medicament. A cannula 56 is mounted on the closed end of the barrel by means of a hub 58.

A safety member in the form of a disc 60 is fitted on the cannula hub 58 so that it is perpendicular to the longitudinal axis of the cannula 56. The radius of the disc 60 should be of such length that when the cannula 56 is placed against the patient's skin surface 62 that the included angle between the cannula 56 and the patient's skin surface 62 and blood vessel 64 will be at least 45° thus making a successful intravenous injection impractical, if not virtually impossible.

It is felt that an impediment such as this to a proper type of intravenous injection will cause the person making the injection to take notice which, when done, will cause such person to immediately realize their error.

The geometry involved in the use of a disc as the safety member is quite simple since an angle of at least 45° is desired. Thus, the length of the cannula and the effective radius of the disc can be equal to produce such an included angle.

Additionally, the disc 60 could have printing thereon to futher clarify the situation once the user has been alerted by the impossibility of achieving the proper angle for intravenous injection.

The safety disc 60 could be affixed to other locations on the cannual end of the barrel, even so, the geometric requirements would remain the same, i.e.: the radius of the disc 60 would necessarily need to be increased if it is moved further away from the end of the cannula 56.

I claim:

1. An I.V. injector having a cylindrical barrel open at one end and closed at the other end by sealing means, a cannula mounted on the closed end outwardly of the sealing means, a plunger slidably carried in the open end of the barrel, a chamber formed in the barrel between the plunger and the sealing means, said chamber being adapted to receive a high concentrate I.V. medicament, and means at the closed end of the barrel to prevent the presentation of the cannula at an included angle between the cannula and the patient's blood vessel of less than 45°, thus preventing proper intravenous injection of the aforesaid medicament into a patient by causing the user to become aware that the usual intravenous injection procedure cannot be followed thereby inducing the user to check the injector, said means comprising spacer means mounted on the closed end of the barrel and extending perpendicularly outward from the longitudinal axis of the barrel a distance whereby the included angle between the cannula and the patient's blood vessel upon presentation of the cannula for injection will be at least 45° thereby making an intravenous injection impractical due to the steep angle of entry.

2. The invention as set forth in claim 1 and wherein the spacer means is a disc.

3. The invention as set forth in claim 2 and wherein said disc has a radius at least as great as the distance from the free end of the cannula to the point where the disc is affixed to the injector.

* * * * *